United States Patent
Landis et al.

(10) Patent No.: US 8,220,458 B2
(45) Date of Patent: Jul. 17, 2012

(54) ARTIFICIAL AIRWAY INTERFACES AND METHODS THEREOF

(75) Inventors: Robert M. Landis, Mountainside, NJ (US); Charles A. Lewis, Carrabelle, FL (US)

(73) Assignee: Mergenet Medical, Inc., Coconut Creek, FL (US)

( * ) Notice: Subject to any disclaimer, the term of this patent is extended or adjusted under 35 U.S.C. 154(b) by 779 days.

(21) Appl. No.: 12/326,094

(22) Filed: Dec. 1, 2008

(65) Prior Publication Data
US 2009/0139530 A1 Jun. 4, 2009

Related U.S. Application Data

(60) Provisional application No. 61/004,746, filed on Nov. 29, 2007.

(51) Int. Cl.
*F16K 31/02* (2006.01)
(52) U.S. Cl. .......... 128/204.23; 128/200.26; 128/207.14
(58) Field of Classification Search ............. 128/200.24, 128/200.26, 207.14; 604/19, 45, 122, 146
See application file for complete search history.

(56) References Cited

U.S. PATENT DOCUMENTS

| | | | | |
|---|---|---|---|---|
| 5,720,276 A | * | 2/1998 | Kobatake et al. | 128/204.18 |
| 7,036,506 B2 | * | 5/2006 | McAuliffe et al. | 128/205.24 |
| 7,152,604 B2 | * | 12/2006 | Hickle et al. | 128/207.14 |
| 2006/0042631 A1 | * | 3/2006 | Martin et al. | 128/207.18 |

* cited by examiner

*Primary Examiner* — Glenn Richman
(74) *Attorney, Agent, or Firm* — Adam C. Underwood, Esq.; Carey Rodriguez Greenberg O'Keefe, LLP (57) ABSTRACT

Embodiments of the present invention provide a device, system and method for providing artificial airway interfaces for use in the treatment of respiratory conditions and in assisted respirations. In an embodiment of the invention, an artificial airway interface for a non-sealing respiratory gas delivery system that directs a jet of gas into the artificial airway is provided. In another embodiment, an artificial airway interface for a non-sealing respiratory gas delivery system that allows for conductance of pressurized respiratory gasses and at least one of a sensor and port for collecting at least one of data and respiratory gas samples is provided. The artificial airway interface can further include an outflow variable restrictor.

19 Claims, 13 Drawing Sheets

ARTIFICIAL AIRWAY INTERFACES AND METHODS THEREOF

CROSS-REFERENCE TO RELATED APPLICATIONS

This patent application claims the benefit of U.S. Provisional Patent Application Ser. No. 61/004,746, filed on Nov. 29, 2007, the entire teachings of which are incorporated by reference herein.

BACKGROUND OF THE INVENTION

1. Statement of the Technical Field

The present invention relates to artificial airways and methods therefor, for example, for use in the treatment of respiratory conditions and in assisted respirations, and more particularly for non-sealing gas delivery systems.

2. Description of the Related Art

Artificial airways can be used when a patient requires breathing assistance, or has a deformity or an injury of the airway. Some conventional artificial airways include endotracheal tubes (ET), nasotracheal tubes and tracheotomy tubes. Such artificial airways can be deployed to provide that a patient's airway remains open and to provide access to the lungs for managing or assisting the respiration of the patient. These artificial airways can be used with or without mechanical respiratory ventilation or assistance.

One limitation created by the use of artificial airways is that artificial airways bypass the body's normal upper respiratory tract where inhaled air is warmed and humidified. Exposure of the lower respiratory tract and lungs to dry and or cool air can cause damage to the lower respiratory tract, the lungs and worsen the patient's respiratory condition. The upper respiratory tract also serves as a defense mechanism for the lungs by capturing particles, allergens and pathogens, and preventing their entry into the lower airway.

Figure 1:
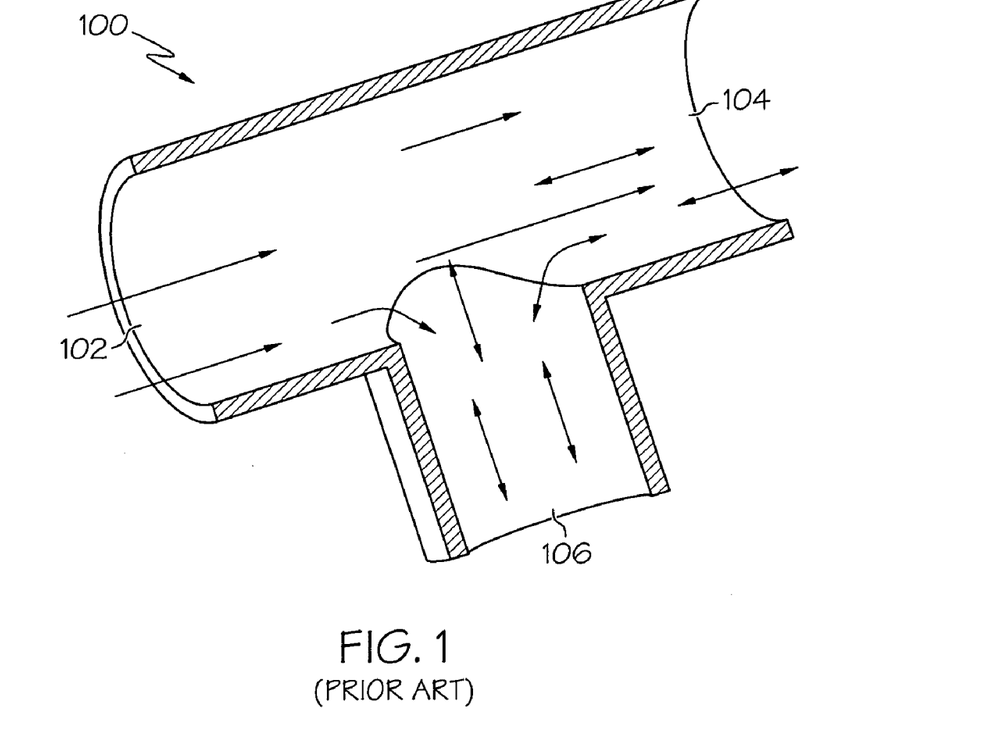
FIG. 1 is a three-dimensional cross sectional view of a conventional tee connector for delivering breathing gasses to an artificial airway.

When a patient is breathing through an artificial airway without the assistance of mechanical ventilation, one standard practice is to supply heated humidity by attaching a Tee fitting to the tube adapter and adding a steady flow of aerosol or heated humidity over the opening of the artificial airway, which is particularly important when delivering oxygen or other anhydrous gas. FIG. 1 illustrates the general format of a convention tee connection 100 for delivery of gas through an artificial airway when a patient is breathing spontaneously. The inlet 102 typically attaches to gas supply (not shown), the artificial airway fitting is typically a 15 mm female fitting, and excess supply gas and exhaled breath from conduit 106 to/from the patient exits to the room through outlet 104.

When the patient inhales using a conventional interface 100 (depending on the inspiratory flow rate and the humidity flow rate) the inhaled gas may be a mixture of room air and therapeutic air/oxygen. Room air may contain particles including pathogens which bypass the normal upper airway. An extension tube may be placed on the exit outflow of the Tee fitting to act as a reservoir for delivered gasses, but this increases the patient's dead air space, and still may not prevent room air from entering the airway. The added dead space may also cause carbon dioxide ($CO_2$) retention, which is undesirable.

SUMMARY OF THE INVENTION

Embodiments of the present invention address deficiencies of the art in respect to artificial airway interfaces and provide a novel and non-obvious device, system and method for providing artificial airway interfaces for use in the treatment of respiratory conditions and in assisted respirations. In an embodiment of the invention, an artificial airway interface can be provided. In accordance with an embodiment of the present invention, an artificial airway interface for a non-sealing respiratory gas delivery system that directs a jet of gas into the artificial airway is provided. In one aspect of the embodiment, the artificial airway interface can include a diverter wall that separates the inflow gases from the outflow gases. In another embodiment, an artificial airway interface for a non-sealing respiratory gas delivery system that allows for conductance of pressurized respiratory gasses and at least one of a sensor and port for collecting at least one of data and respiratory gas samples is provided. The artificial airway interface can further include an outflow variable restrictor.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION

Aspects of an artificial airway interface are disclosed in the following description and related drawings directed to specific embodiments of an artificial airway interface for use in the treatment of respiratory conditions and in assisted respirations. Alternate embodiments may be devised without departing from the spirit or the scope of the artificial airway interface. Additionally, well-known elements of exemplary embodiments of the artificial airway interface will not be described in detail or will be omitted so as not to obscure the relevant details of the artificial airway interface. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the artificial airway interface" does not require that all embodiments of the artificial airway interface include the discussed feature, advantage or mode of operation. In the drawings and in the description which follows, the term "proximal", as is traditional will refer to the end of the device or apparatus which is closest to the individual or patient, while the term "distal" will refer to the end of the device or apparatus which is furthest from the individual or patient.

Embodiments of the present invention address deficiencies of the art in respect to artificial airway interfaces and provide a novel and non-obvious device, method and system for providing an artificial airway interface for use in the treatment of respiratory conditions and in assisted respirations. Embodiments of the present invention provide a device, system and method for providing artificial airway interfaces for use in the treatment of respiratory conditions and in assisted respirations. In an embodiment of the invention, an artificial airway interface for a non-sealing respiratory gas delivery system that directs a jet of gas into the artificial airway is provided. In another embodiment, an artificial airway interface for a non-sealing respiratory gas delivery system that allows for conductance of pressurized respiratory gasses and at least one of a sensor and port for collecting at least one of data and respiratory gas samples is provided. The artificial airway interface can further include an outflow variable restrictor.

Figure 2:
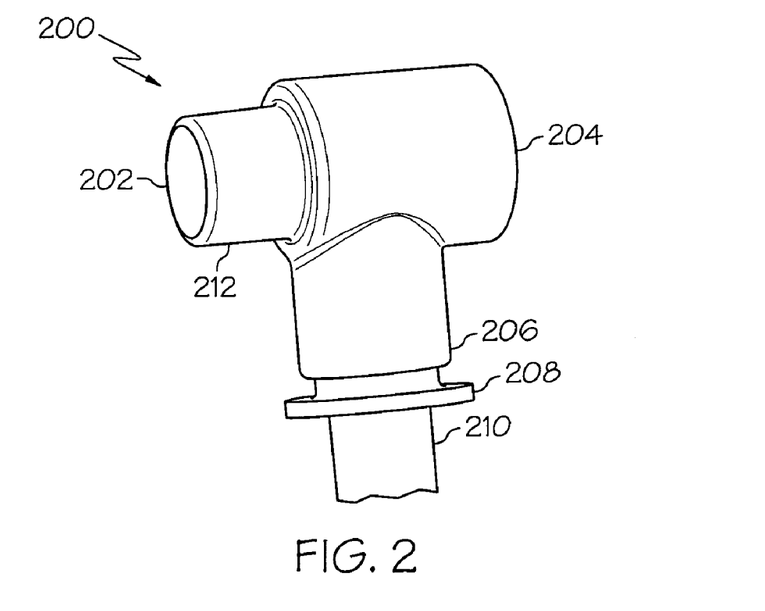
FIG. 2 is a three-dimensional perspective view of a tee connector for attachment to an artificial airway, which is constructed in accordance with an embodiment of the present invention.

Referring to FIG. 2, a three-dimensional perspective view of an interface (e.g., a tee connector) for attachment to an artificial airway can be constructed in accordance with an embodiment of the present invention. The artificial airway interface 200 can include an inlet 202, e.g., a supply gas inlet, an outlet conduit 204, e.g., an exhalation outlet conduit and another conduit 206 for connection 208 to the artificial airway 210. FIG. 2 illustrates that the artificial airway interface 200 (e.g., a tee connector) can include a male inlet fitting 212 for connecting to a gas/air supply (not shown). The tee 200 attaches to the artificial airway fitting 210 at connection 208, but has a different internal structure than the conventional tee connector illustrated in FIG. 1.

Figure 3:
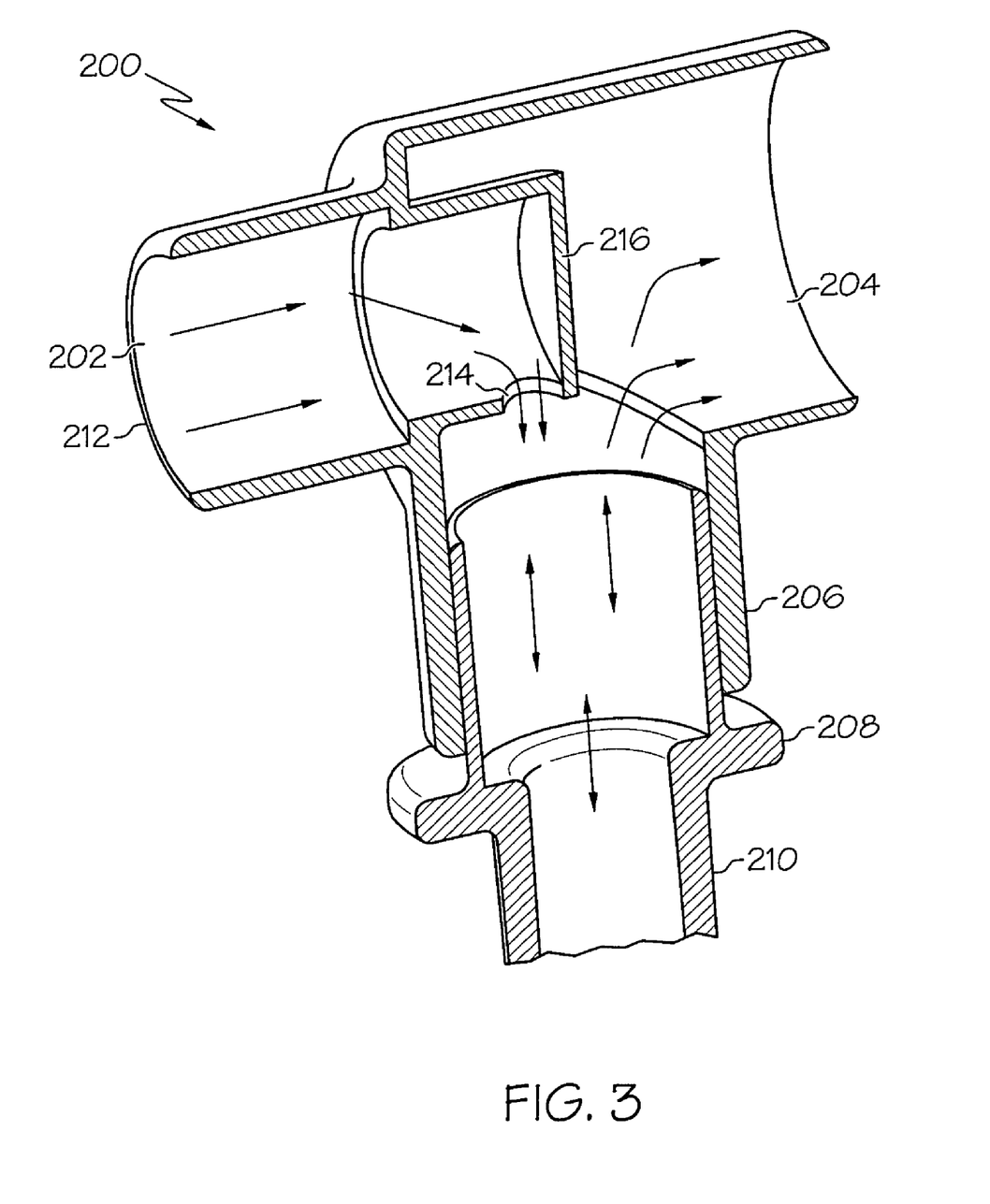
FIG. 3 is cross-sectional view of the tee connector of FIG. 2, which is constructed in accordance with an embodiment of the present invention.

Referring to FIG. 3, a cross-sectional view of the artificial airway (tee) connector of FIG. 2 is illustrated. Instead of a straight Tee configuration as illustrated by the conventional Tee connector of FIG. 1, the airway interface 200 can include an internal structure, e.g., high flow orifice 214 and flow diverter wall 216 that redirects the breathable gas downward towards the artificial airway 210. In embodiments, the high flow orifice 214 directs the gas flow. The orifice 214 can be smaller than the diameter of the artificial airway 210 that can assist with the formation of a gas jet or turbulence. The formation of a gas jet or turbulence in the breathable gas can have the advantage of generating an increase in airway pressure, which for some patients acts to reduce the work of breathing. Higher flows of gas delivery therapy can create a stronger jet. In embodiments, the outflow tract of the orifice can be configured to help promote the formation of a jet.

During expiration, the gas jet or turbulence can create some positive airway pressure which can help the patient maintain open airways and help to empty the lungs for patients with emphysema. This action is similar to positive end expiratory pressure (PEEP) which is often used in conjunction with mechanical ventilation. In addition, this action also can simulate pursed lipped breathing—a natural compensatory breathing pattern often seen when patients have chronic obstructive pulmonary disease (COPD). Furthermore, the jet of respiratory gas also can flush the end respiratory exhalation to thus decrease the dead air space, and can help to limit carbon dioxide retention in some patients. An extension to a distal arm of the interface, (the outflow tract) can be added to increase dead air space if so desired.

By directing sufficient flow into the artificial airway 210, it is possible to provide enough flow to completely satisfy the patient's inspiratory flow rate and thereby avoid entrainment of room air to dilute the delivered breathing gases. This important feature can provide two benefits. First, it can give the clinician confidence that the patient is breathing the gasses being delivered and not an unknown mixture of room air. Second, it also can serve to minimize the possibility of air containments being inhaled. Patients with artificial airways often can be more vulnerable to containments causing infection.

Figure 4:
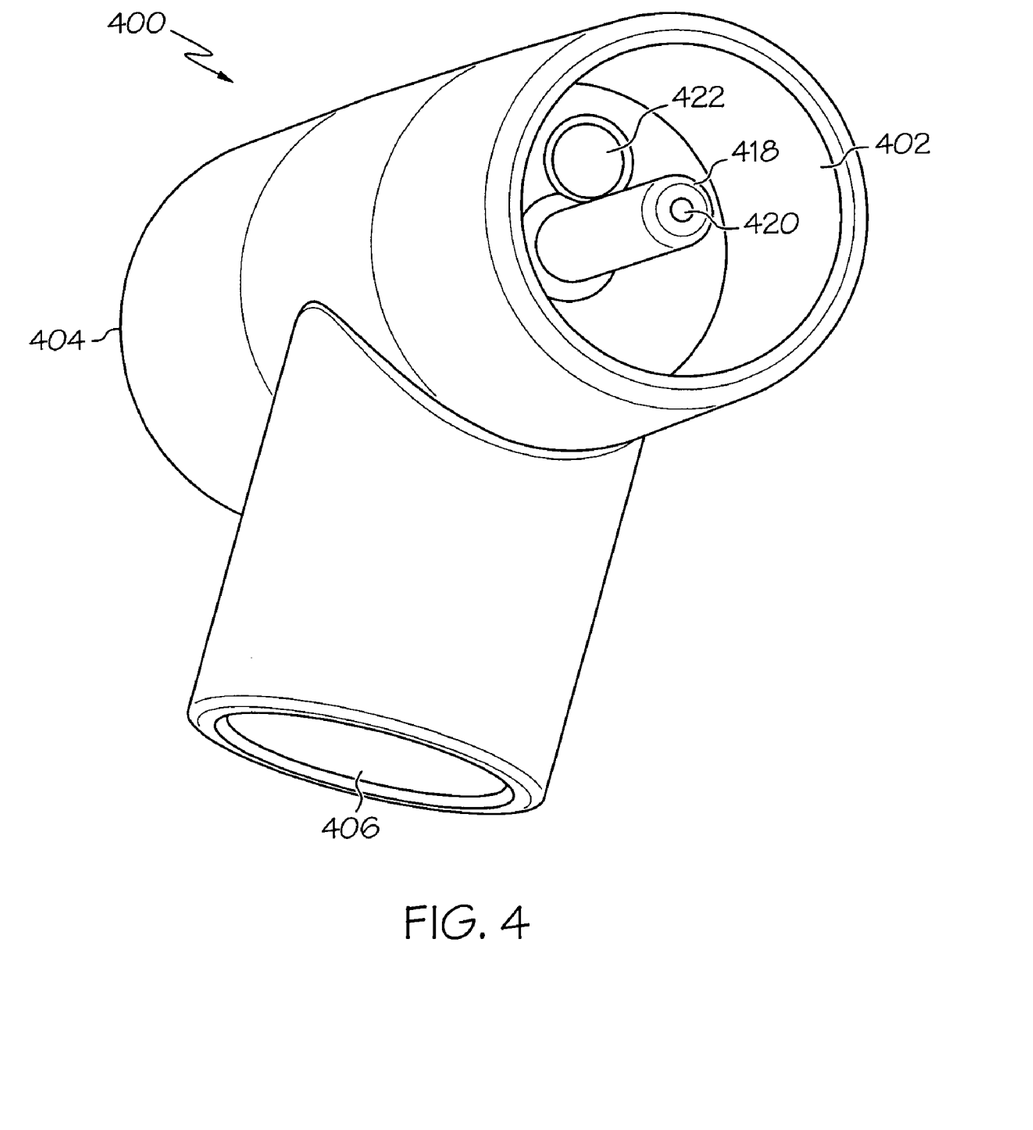
FIG. 4 is a perspective view of a tee connector for attachment to an artificial airway that includes a sampling port with a coaxial fitting which is constructed in accordance with an embodiment of the present invention.

FIG. 4 is a perspective view of a tee connector for attachment to an artificial airway that includes a sampling port with a coaxial fitting. In embodiments, the artificial airway interface 400 can include a coaxial inlet 402 that can provide a first conduit or port 422 for high flow respiratory gasses and a second conduit or port 420 for gathering patient status information. Among the uses of the second conduit or port 420 are to collect information about the patient, patient's breathing, the patient's physiologic status, and device status including the pressure of gases delivered. The second conduit or port 420 can be used to sample exhaled gases such as end expiratory $CO_2$ levels, pressure, temperature, or other variables.

Figure 5:
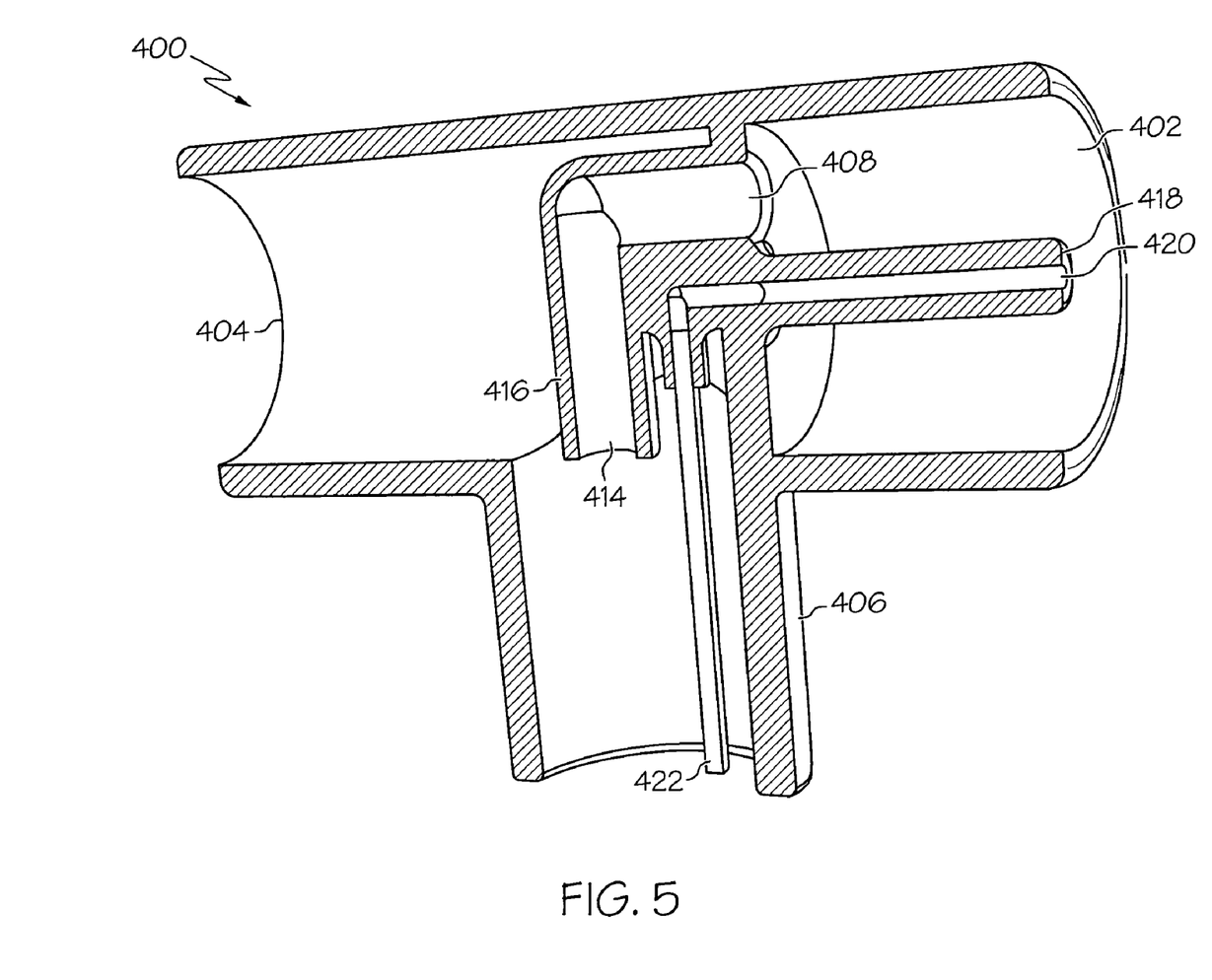
FIG. 5 is a cross-sectional view of the tee connector of FIG. 4, which is constructed in accordance with an embodiment of the present invention.
Figure 6:
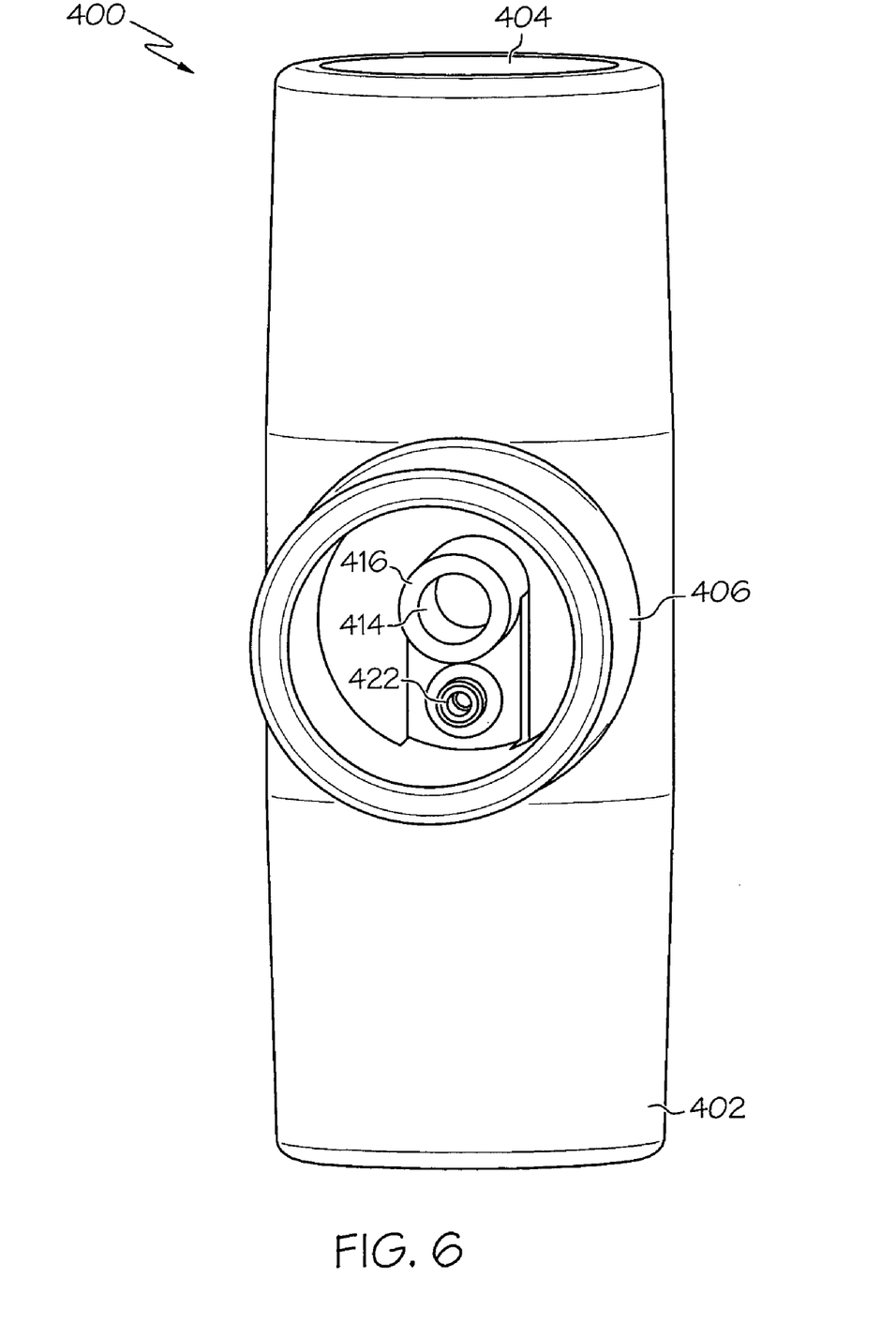
FIG. 6 is a bottom view of the tee connector of FIG. 4, which is constructed in accordance with an embodiment of the present invention.

FIG. 5 is a cross-sectional view of the tee connector of FIG. 4, which is constructed in accordance with an embodiment of the present invention. FIG. 6 is a bottom view of the tee connector of FIG. 4. Similar to connector 200, connector 400 has an inlet conduit 402, an outlet conduit 404, and an artificial airway conduit 406. FIG. 5 illustrates that the artificial airway connector 400 can include a second conduit or port 420. The second conduit or port 420 can be connected to a pressure sensor (not shown) to provide monitoring of a patient's airway pressure and respiratory cycle. In embodiments, a port orifice 422 of second conduit or port 420 can be extended into the artificial airway fitting. Referring to FIGS. 4 and 5, first port 422 has an inlet portion 408 that is parallel (i.e. coaxial) to inlet conduit 402 and to second port 420. First port 422 also has an outlet portion 414 with a first port outlet wall 416 that is parallel (i.e. coaxial) to artificial airway conduit 406. As can be understood from FIG. 5, first port 422 acts as a diverter as it directs gas flow towards artificial airway conduit 406 and not towards outlet conduit 404. Second port 420 has a first side 418 and a second side defined by port orifice 422. First side 418 can be located in inlet conduit 402 and second side 422 can be located in artificial airway conduit 406. Therefore second port 420, which was previously described as used for sampling, can connect to the gas supply side via inlet conduit 402 in one direction and sense in a different direction (i.e. at second side 422 in artificial airway conduit 406). The use of an airway pressure sensor (not shown) can provide feedback to give the added advantage of allowing the clinician to titrate the flow rate and achieve the desired airway pressures. The airway pressure sensor also can provide information to assure the clinician that the flow rate is sufficient to meet the inspiratory demand or flow rate of the patient. By meeting inspiratory demand there is a high-level of confidence that the patient breathes only the delivered gas that is not diluted with room air during inhalation, and that the patient is not breathing air with contaminants.

Information collected at the artificial airway interface 400 can be used to help determine the optimal therapeutic requirements for gas delivery or for patient monitoring. This gives information which in the present state of the art is not available for patients with artificial airways breathing on their own via open airway systems. Information collected at the airway interface may be used to control the flow rate during the respiratory cycle where the flow rate can change with inspiration and expiration. The artificial airway interface 400 may also include a probe or a port for a probe. The probe may include sensors for oxygen, carbon dioxide, or other gases, for pressure, temperature, collection of exhaled breath condensate or for other measurements. One embodiment allows for use with optical fibers. Optical fibers have an advantage of small size, such that these optical fibers do not greatly impede respiratory flow. Optical fibers can be used for a probe or in conjunction with one or more sensors. The probe may be displaced within the housing of the interface 400, or configured so that it may be advanced into or even beyond the artificial airway.

In embodiments, an outflow arm is configured to fit to a connector. This connector may be an extension that can act as a reservoir, which can increase dead air space if desired. The interface can include one or more swivels which allow directional motion for connection to the artificial airway and to the supply, probe and outlet ports.

Figure 7:
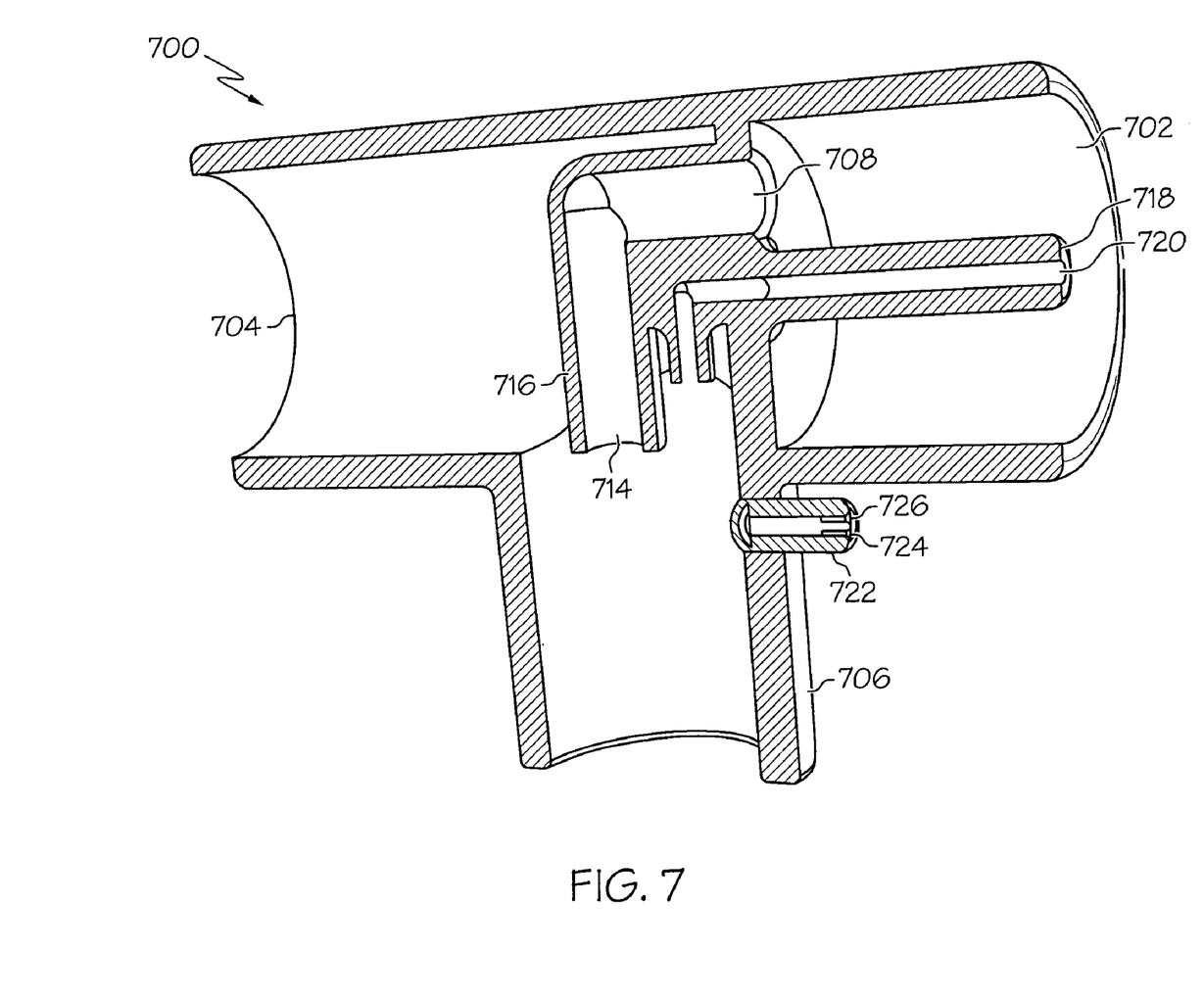
FIG. 7 is a perspective view of a tee connector for attachment to an artificial airway that includes a second general sensor port, which is constructed in accordance with an embodiment of the present invention.
Figure 8:
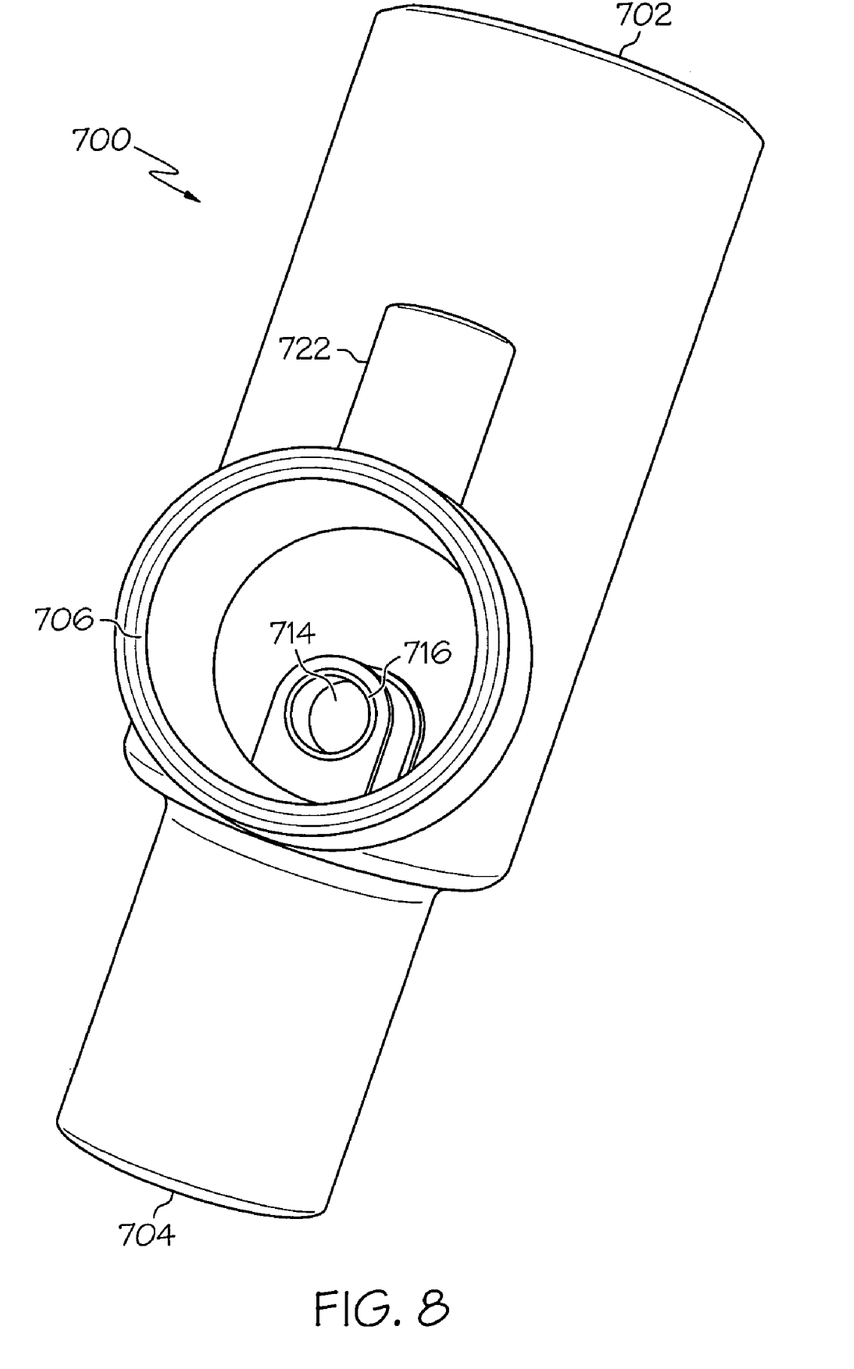
FIG. 8 is a bottom view of the tee connector of FIG. 7, which is constructed in accordance with an embodiment of the present invention.

FIG. 7 is a perspective view of a tee connector for attachment to an artificial airway that includes a second general sensor port, which is constructed in accordance with an embodiment of the present invention. In embodiments, the artificial airway connector 700 can be configured similar to the artificial airway connector 400 with the exception of a second sensor port 722. In embodiments, the second sensor port 722 can include sensors for oxygen, carbon dioxide, or other gases, for pressure, temperature, collection of exhaled breath condensate or for other measurements. FIG. 8 is a bottom view of the tee connector of FIG. 7, which illustrates that the artificial airway connector 700 can be without the measurement lumen 720. Similar to connector 400, connector 700 has an inlet conduit 702, an outlet conduit 704, and an artificial airway conduit 706. Similar to connector 400, connector 700 has a first port with an inlet portion 708 and an outlet portion 714 with a first port outlet wall 716. Measurement lumen 720 can have a first side 718 and a second side that can be located in artificial airway conduit 706. This embodiment illustrates the ability to have at least two different sampling ports (i.e. measurement lumen 720 and second sensor port 722). Second sensor port 722 can further have connecting locations 724 and 726.

Figure 9:
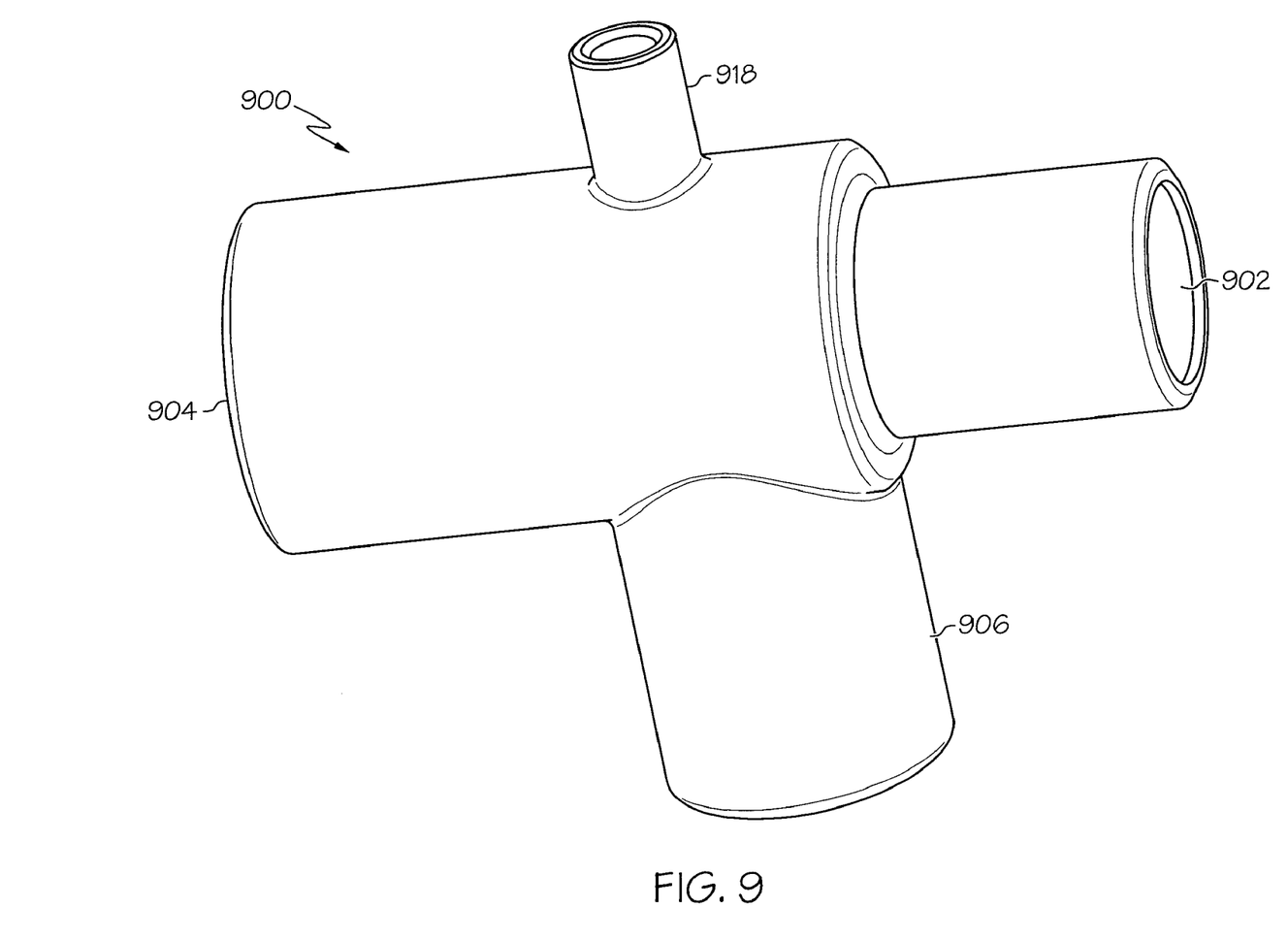
FIG. 9 is a perspective view of a tee connector for attachment to an artificial airway that includes a sampling port with an external sample port fitting according to one embodiment of the invention.
Figure 10:
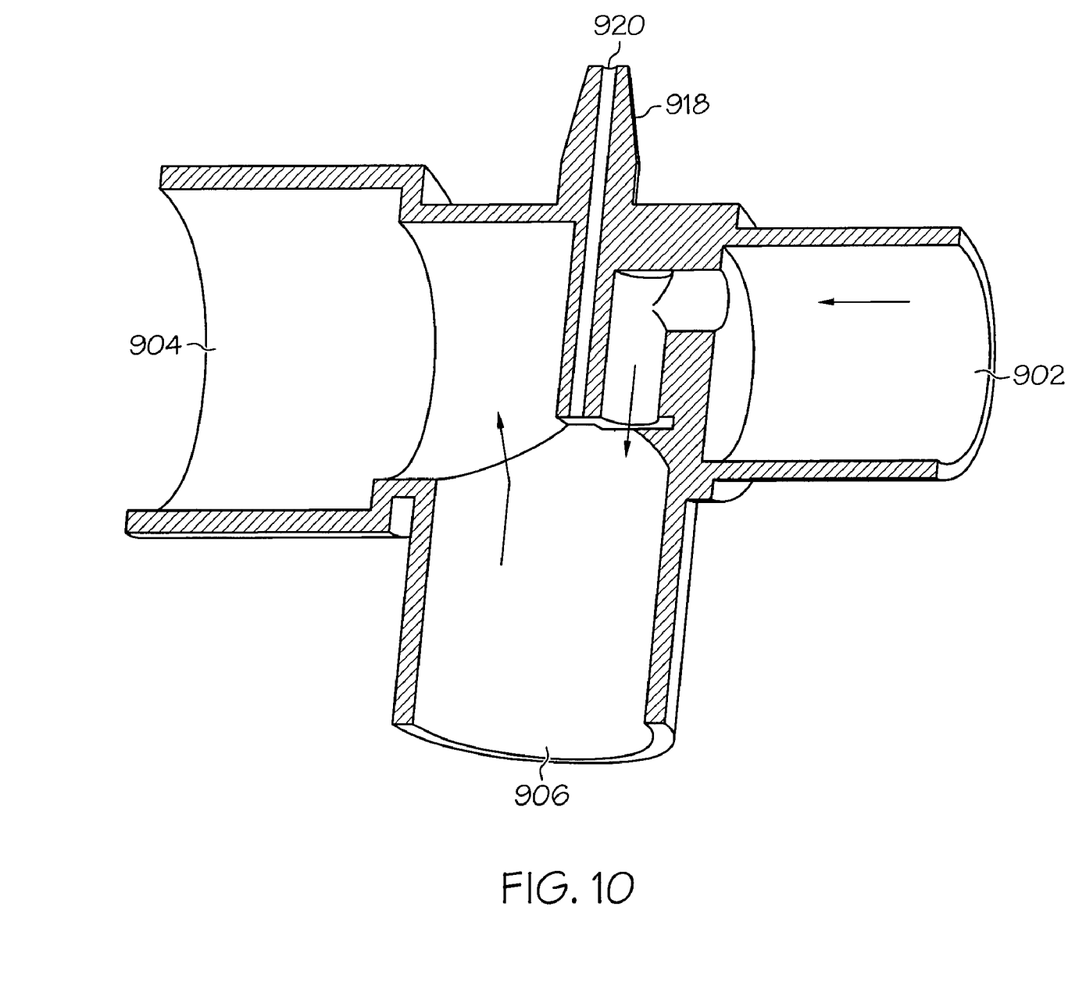
FIG. 10 is a is cross-sectional view of the tee connector of FIG. 9, which is constructed in accordance with an embodiment of the present invention.

FIG. 9 is a perspective view of a tee connector for attachment to an artificial airway that includes a sampling port with an external sample port fitting according to one embodiment of the invention. Similar to connector 400, connector 900 has an inlet conduit 902, an outlet conduit 904, and an artificial airway conduit 906. In embodiments, the external sample port fitting 918 is located external to the artificial airway interface 900. FIG. 10 is a cross-sectional view of the tee connector of FIG. 9 and illustrates another configuration of an artificial airway interface 900 in which the probe attachment port 920 is on the outside of the artificial airway interface 900 to collect information about the patients breathing, the patients physiologic status, and device status. A probe may be used to sample exhaled gases such as end expiratory $CO_2$ levels, pressure, temperature, or other variables for artificial airways.

Figure 11:
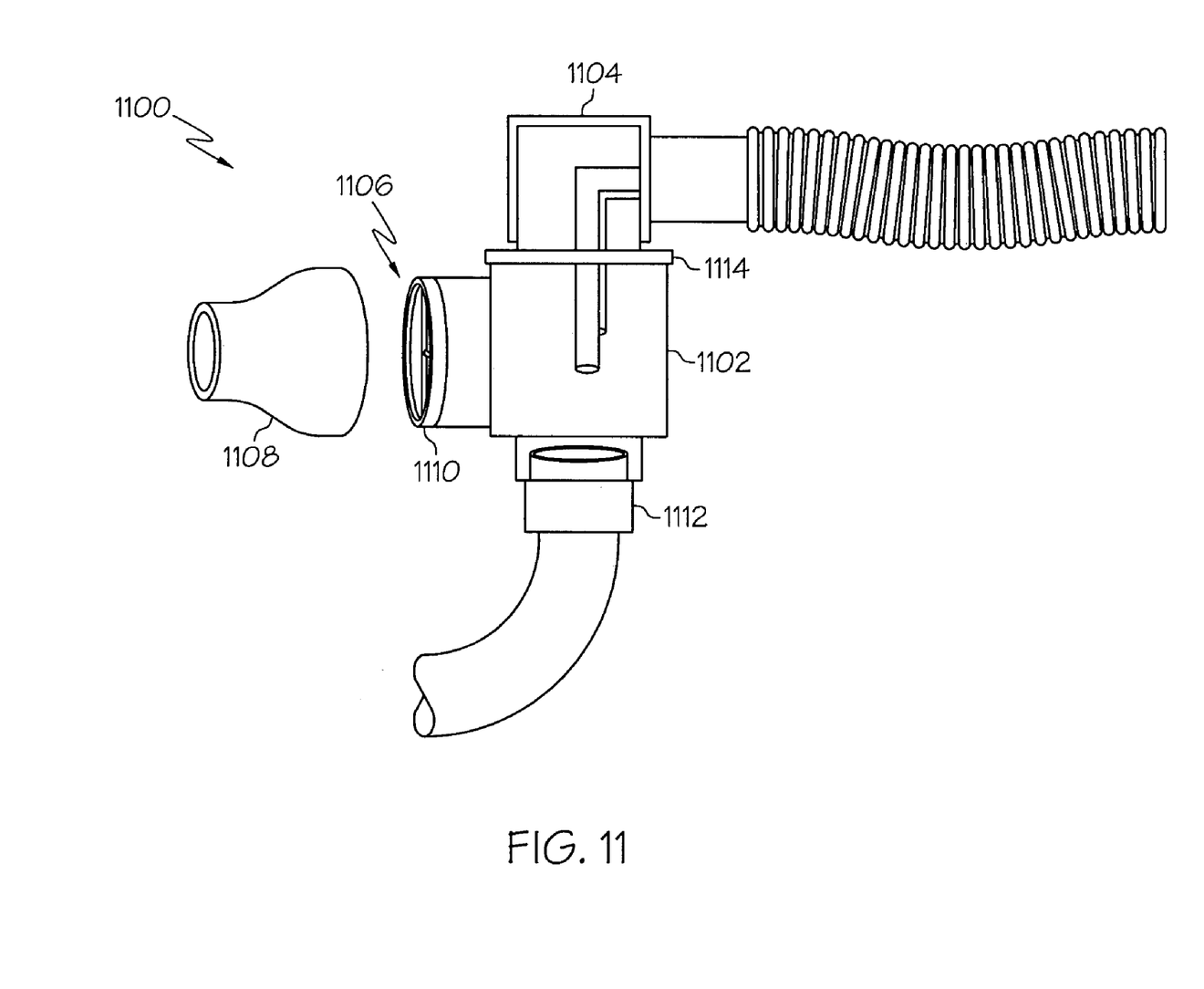
FIG. 11 is a schematic drawing of a tee connector for attachment to an artificial airway that is connected to an artificial airway and a mechanical respiratory source, the tee connector includes outflow restrictors, which is constructed in accordance with an embodiment of the present invention.

FIG. 11 is a schematic drawing of a tee connector for attachment to an artificial airway that is connected to an artificial airway and a mechanical respiratory source, the tee connector includes outflow restrictors, which are constructed in accordance with an embodiment of the present invention. Interface 1100 is shown with a ventilated flap valve 1110. A reducer 1108 is shown in FIG. 11 which will allow connection to standard size fittings and tube extensions. The vent of the valve 1100 is shown in the open (vented flap not in use) position 1122 in FIG. 12C and in the closed position 1120 in FIG. 12B. The vent opening can be configured to be larger than the area of the cross section of the artificial airway 1112 so that it does not create additional resistance to expiration even with the additional flow of the high flow therapy.

Figure 12A:
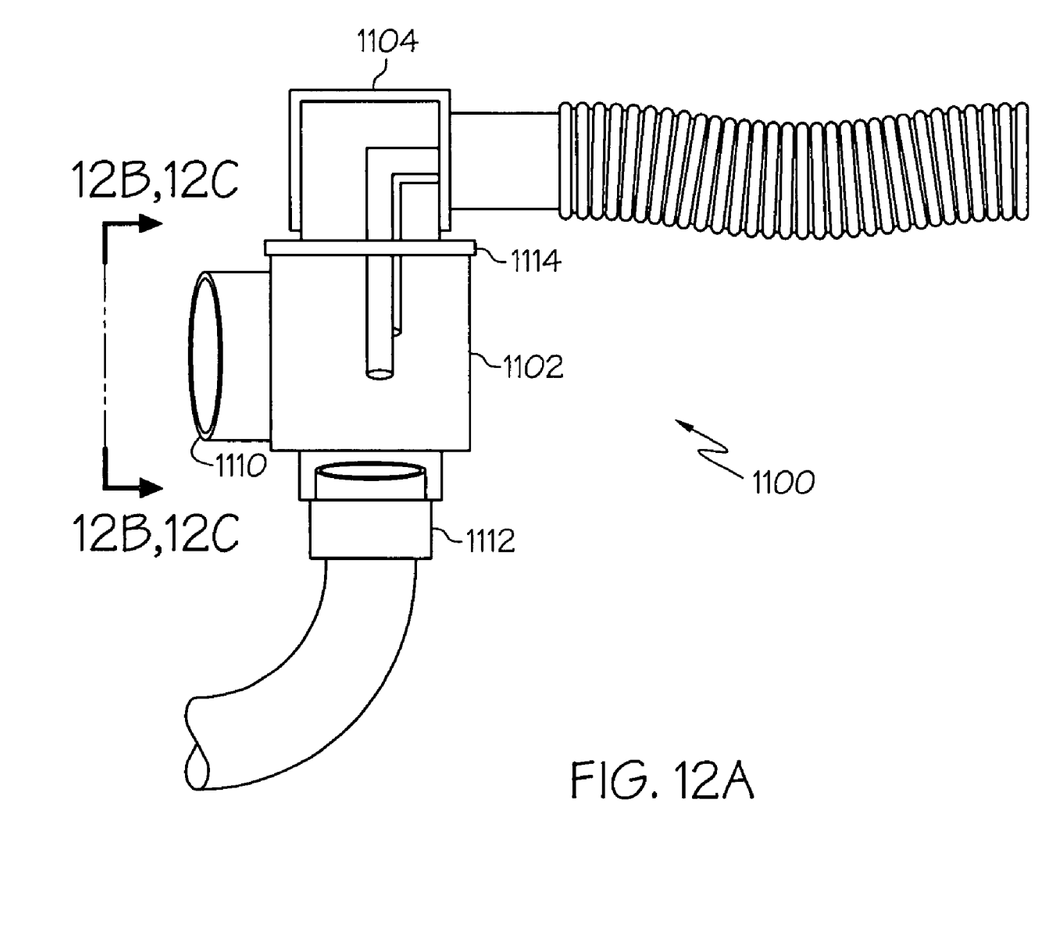
FIG. 12 is a schematic drawing of a tee connector for attachment to an artificial airway that is connected to an artificial airway and a mechanical respiratory source, the tee connector includes a ventilated flap valve, which is constructed in accordance with an embodiment of the present invention; and, FIGS. 13A-13G are schematic drawings that of the vented flap valve of the tee connectors illustrated in FIGS. 11 and 12, which are constructed in accordance with embodiments of the present invention.
Figure 12B:
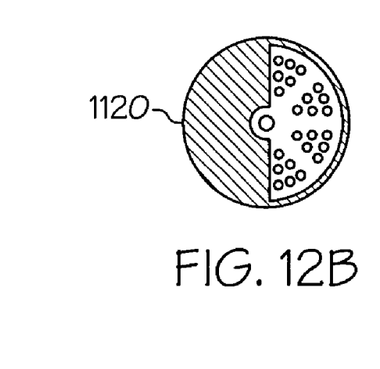
Figure 12C:
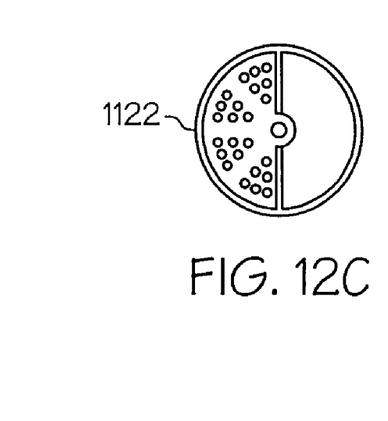

FIG. 12 is a schematic drawing of a tee connector for attachment to an artificial airway that is connected to an artificial airway and a mechanical respiratory source, the tee connector includes a ventilated flap valve, which is constructed in accordance with an embodiment of the present invention.

Figure 13A:
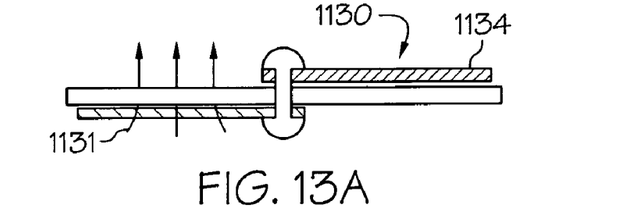
Figure 13B:
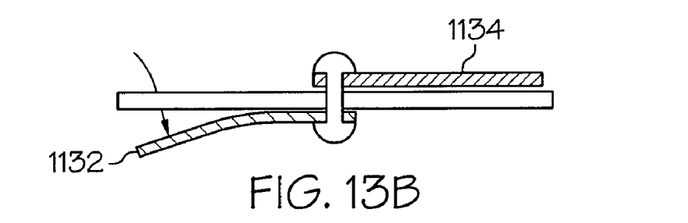
Figure 13C:
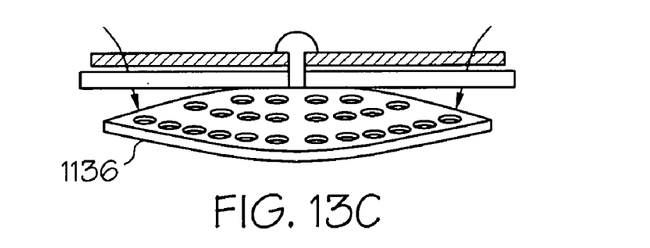
Figure 13D:
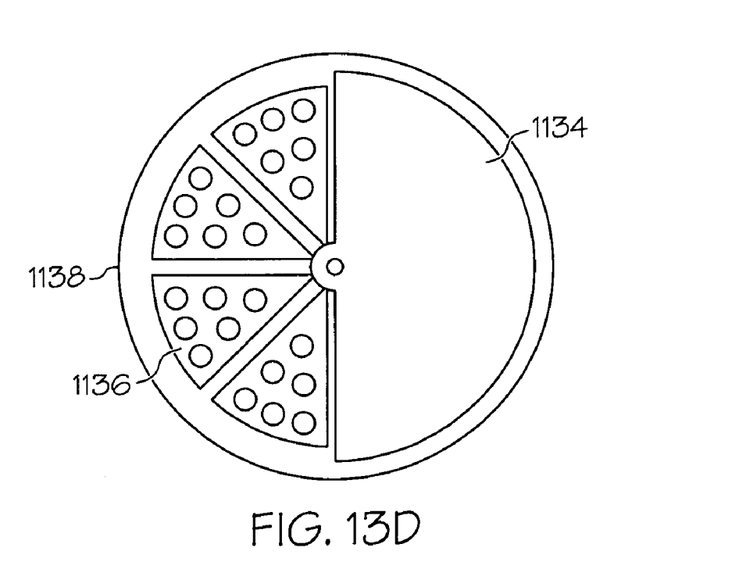

FIGS. 13A-13G are schematic drawings of the vented flap valve of the tee connectors illustrated in FIGS. 11 and 12. The vented flap valve 1130 is shown in its fixed position in FIG. 13A, and arrows 1131 show the vented flap valve position in use during expiration and gas flow exhaust. This illustrates the valve 1130 in the position for maximal restriction of gas egress and the maximal positive end expiratory pressure (PEEP). Air escapes as a result of the holes in the flap valve. Valves 1130 can be configured for different amounts of ventilation during expiration by the size and number of holes. For example, FIGS. 13B and 13C illustrate two views of flap valve 1110 in an open position as would occur if the air supply from the supply source was insufficient for respiratory demand during inhalation. This could occur during machine failure, or if the gas delivery rate was set too low. The flap valve 1110 acts as a safety feature to assure that the patient can get sufficient air in the case of a setting error or machine failure. FIG. 13D illustrates a top down view of the valve assembly 1110 with the cover 1134 in the closed position.

Figure 13E:
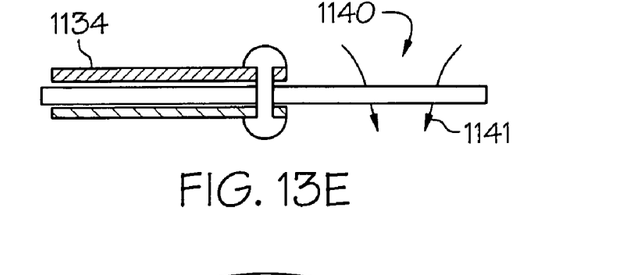
Figure 13F:
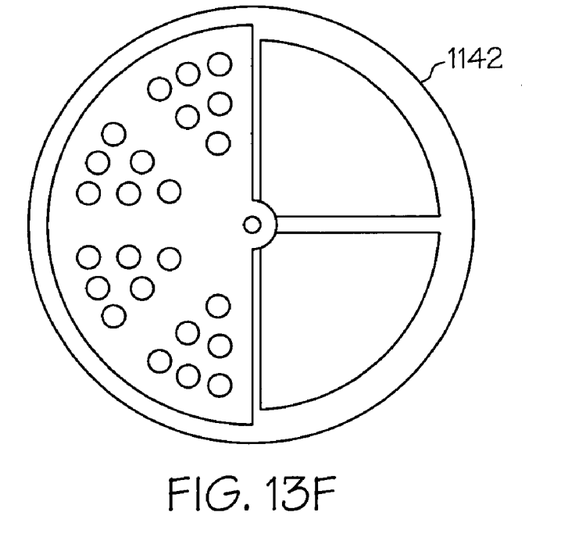
Figure 13G:
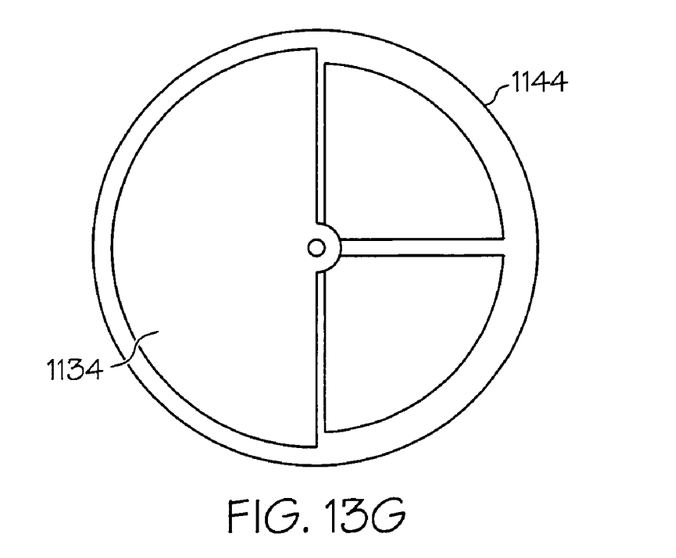

Cover 1134 is configured in this embodiment to rotate to be closed as shown in FIG. 13D, or open as illustrated in FIGS. 13E, 13F and 13G, or to be partially open.

FIGS. 13E, 13F and 13G illustrate a cutaway side view of the valve assembly 1110 in the full open position where the flap valve 1110 is not in use. The arrows 1141 in FIG. 13E illustrate gas flow. FIG. 13F illustrates the underside (the airway side) with the flap valve material 1136 covered by the cover 1134. FIG. 13G illustrates the outer cover 1134 component which is configured to rotate to vary the opening of the assembly. By rotating the cover 1134, shown as dark grey on the superior surface of the valve assembly 1110, the PEEP may be adjusted.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims, which are to be accorded with the broadest interpretation so as to encompass all such modifications and similar structures.

Therefore, the above-described embodiments should be regarded as illustrative rather than restrictive. Accordingly, it should be appreciated that variations to those embodiments can be made by those skilled in the art without departing from the scope of the nasal mask assembly as defined by the following claims.

The Abstract is provided to comply with 37 C.F.R. §. 1.72(b) to allow the reader to quickly ascertain the nature and gist of the technical disclosure. The Abstract is submitted with the understanding that it will not be used to interpret or limit the scope or meaning of the claims.

We claim:

1. A connector configured for connecting to an artificial airway, the connector comprising:
   an inlet conduit configured to receive supplied respiratory gas;
   an outlet conduit configured to allow exhaled gas to exit to atmosphere during use;
   an artificial airway side conduit configured to couple to an artificial airway; and,
   an internal diverter structure configured to redirect the supplied respiratory gas from the inlet conduit towards the artificial airway side conduit and away from the outlet conduit during use.

2. The connector of claim 1, wherein the internal diverter structure is a gas port located in the inlet conduit.

3. The connector of claim 1, further comprising a separate internal gas port located in the inlet conduit.

4. The connector of claim 1, further comprising at least one sensing conduit.

5. A connector configured for connecting to an artificial airway, the connector comprising:
   an inlet conduit configured to receive supplied respiratory gas;
   an outlet conduit configured to allow exhaled gas to exit to atmosphere during use;
   an artificial airway side conduit configured to couple to an artificial airway; and,
   a separate internal gas port located in the inlet conduit that further receives the supplied respiratory gas and directs it towards the artificial airway side conduit.

6. The connector of claim 5, wherein the cross-sectional area of the gas port is less than the cross-sectional area of the inlet conduit.

7. The connector of claim 5, wherein the cross-sectional area of the gas port is less than the cross-sectional area of the artificial airway side conduit.

8. The connector of claim 5, wherein the gas port is structured to jet the gas into the artificial airway side conduit.

9. The connector of claim 8, wherein the jetted gas increases the pressure in the artificial airway side conduit.

10. The connector of claim 8, wherein the jetted gas increases the pressure in the artificial airway side conduit in order to one of minimize and eliminate entrainment of ambient air through the outlet conduit during use.

11. The connector of claim 5, further comprising at least one sensing conduit.

12. The connector of claim 5, wherein a portion of the internal structure of the connector is configured to redirect the supplied respiratory gas from the inlet conduit towards the artificial airway side conduit and away from the outlet conduit during use.

13. The connector of claim 5, further comprising an outflow variable restrictor.

14. A connector configured for connecting to an artificial airway, the connector comprising:
   an inlet conduit configured to receive supplied respiratory gas;
   an outlet conduit configured to allow exhaled gas to exit to ambient during use;
   an artificial airway side conduit configured to couple to an artificial airway; and,
   a sensing conduit.

15. The connector of claim 14, wherein the sensing conduit has an inlet portion in a first direction and an outlet portion in a second direction.

16. The connector of claim 14, wherein the sensing conduit is internal to the connector.

17. The connector of claim 14, wherein the sensing conduit has an inlet potion that is parallel to the inlet conduit.

18. The connector of claim 14, wherein the connector has at least a second sensing conduit.

19. The connector of claim 14, wherein the sensing conduit facilitates measuring pressure in one of the artificial airway side conduit and the artificial airway during use.

* * * * *